US010787407B2

(12) United States Patent
Crawford et al.

(10) Patent No.: US 10,787,407 B2
(45) Date of Patent: Sep. 29, 2020

(54) METHODS AND SYSTEMS FOR ENERGY-EFFICIENT DRYING OF CO-PRODUCTS IN BIOREFINERIES

(71) Applicant: Energy Integration, Inc., Boulder, CO (US)

(72) Inventors: Lynn Allen Crawford, Aurora, CO (US); William Bryan Schafer, III, Boulder, CO (US)

(73) Assignee: ENERGY INTEGRATION, INC., Boulder, CO (US)

( * ) Notice: Subject to any disclaimer, the term of this patent is extended or adjusted under 35 U.S.C. 154(b) by 0 days.

(21) Appl. No.: 16/721,896

(22) Filed: Dec. 19, 2019

(65) Prior Publication Data
US 2020/0247738 A1 Aug. 6, 2020

Related U.S. Application Data

(60) Provisional application No. 62/800,044, filed on Feb. 1, 2019, provisional application No. 62/857,619, filed on Jun. 5, 2019.

(51) Int. Cl.
*C07C 29/80* (2006.01)
*B01D 3/00* (2006.01)
(Continued)

(52) U.S. Cl.
CPC .............. *C07C 29/80* (2013.01); *B01D 3/001* (2013.01); *B01D 3/007* (2013.01); *B01D 5/006* (2013.01); *B01D 5/0075* (2013.01); *C07C 29/82* (2013.01)

(58) Field of Classification Search
CPC ......... C07C 29/80; C07C 29/82; B01D 3/001; B01D 3/007; B01D 5/006; B01D 5/0075;
(Continued)

(56) References Cited

U.S. PATENT DOCUMENTS 3,721,568 A * 3/1973 Wilson ...................... A23L 3/46
426/452
4,309,254 A * 1/1982 Dahlstrom ................ B01D 1/26
159/47.1
(Continued)

FOREIGN PATENT DOCUMENTS

GB        1316896        5/1973

OTHER PUBLICATIONS

Monceaux, D.A., et al., Dryhouse technologies and DDGS production, Chapter 21, Reprinted from the Alcohol Textbook 5th Edition 2009 with permissin form Lallemand Ethanol Technology and Nottingham University Press, pp. 303-332 (Year: 2009).*
(Continued)

Primary Examiner — Yate' K Cutliff
(74) Attorney, Agent, or Firm — O'Connor & Company; Ryan P. O'Connor

(57) ABSTRACT

A method is disclosed for improving the energy efficiency of biorefinery drying operations through integration of a dryer that utilizes the heat of condensation of process vapors to dry material whose emissions are captured with energy recovery. The dryer separates clean process vapors (e.g., ethanol) and steam from vapors containing volatile organic compounds and entrained materials, to minimize the need for vapor cleanup. An indirect dryer condenses vapors in a tube dryer similar to a steam tube dryer, but utilizing compressed process vapors, transferring the heat to wet material undergoing drying. The resulting exhaust vapors are either directed to a process stage that requires heat (e.g., distillation) and minimizes the need for vapor cleanup or to an out-of-contact heat exchanger that produces vapors for process use, or to another dryer as an additional effect. Mechanical-vapor recompression or thermal-vapor recom-
(Continued)

pression are employed to produce vapors that optimize overall energy recovery.

20 Claims, 3 Drawing Sheets

(51) Int. Cl.
*B01D 5/00* (2006.01)
*C07C 29/82* (2006.01)

(58) Field of Classification Search
CPC ...... F26B 3/04; F26B 3/02; F26B 3/32; F26B 23/001
See application file for complete search history.

(56) References Cited

U.S. PATENT DOCUMENTS

| | | | |
|---|---|---|---|
| 4,340,446 A * | 7/1982 | Crawford | B01D 1/2806 203/19 |
| 4,422,903 A | 12/1983 | Messick et al. | |
| 4,536,258 A | 8/1985 | Huhta-Koivisto | |
| 4,539,076 A | 9/1985 | Swain | |
| 4,585,523 A | 4/1986 | Giddings | |
| 4,617,270 A * | 10/1986 | Anderson | C12F 3/08 426/11 |
| 4,645,569 A | 2/1987 | Akabane et al. | |
| 4,692,218 A | 9/1987 | Houben et al. | |
| 4,746,610 A | 5/1988 | Smith | |
| 5,294,304 A | 3/1994 | Kano et al. | |
| 5,772,850 A | 6/1998 | Morris | |
| 7,257,945 B2 | 8/2007 | Kass et al. | |
| 8,101,217 B2 | 1/2012 | Sovereign et al. | |
| 8,101,808 B2 | 1/2012 | Evanko et al. | |
| 8,114,255 B2 | 2/2012 | Vane et al. | |
| 8,128,787 B2 | 3/2012 | Wynn et al. | |
| 8,283,505 B2 | 10/2012 | Evanko et al. | |
| 8,304,588 B2 | 11/2012 | Evanko et al. | |
| 8,614,077 B2 | 2/2013 | Evanko et al. | |
| 8,535,413 B2 | 11/2013 | Bryan et al. | |
| 9,138,678 B2 | 9/2015 | Huang et al. | |
| 2016/0002131 A1 * | 1/2016 | Glasspool | B01D 1/28 203/18 |
| 2017/0089640 A1 * | 3/2017 | Nakata | F26B 17/32 |
| 2017/0153025 A1 * | 6/2017 | Zhao | B02C 21/00 |

OTHER PUBLICATIONS

International Search Report and Written Opinion, PCT/US2019/067699, dated Feb. 25, 2020.

* cited by examiner

METHODS AND SYSTEMS FOR ENERGY-EFFICIENT DRYING OF CO-PRODUCTS IN BIOREFINERIES

PRIORITY DATA

This patent application is a non-provisional application claiming priority to U.S. Provisional Patent App. No. 62/800,044, filed on Feb. 1, 2019; and U.S. Provisional Patent App. No. 62/857,619, filed on Jun. 5, 2019, each of which is hereby incorporated by reference herein.

FIELD OF THE INVENTION

The present invention generally relates to drying, and methods and systems for improving the energy efficiency of drying operations.

BACKGROUND OF THE INVENTION

Bio-fermentation products, which include biofuels, biochemicals, and co-products such as dried distillers grains, are the result of the investment of significant energy. A biological raw material is grown and then converted by chemical processing to a purified liquid fuel, as well as drying of co-products such as dried distillers grains. Each step requires energy-intensive stages which include distillation of the biofuel and co-product drying. Conventional, first-generation methods employed at bio-distillery plants expend significant energy in distillation and drying, with the total process energy being about one-third of the energy contained in the produced biofuel. The inefficiencies of these methods negatively impact producer economics as well as the environmental footprint ascribed to the process.

The process energy consumed in distilling and co-product drying typically constitutes the largest energy requirement in the production life cycle for ethanol or other fermentation products. The distillation energy in a standard bio-fermentation distillery represents from 40% to 60% of the total process energy. "Total process energy" refers to direct heating of processes by burning fuels, plus the electrical energy required for mechanical power used in pumping, stirring, grinding, etc.

Distillation systems are designed to meet a quality requirement appropriate for product market quality while meeting regulatory environmental emission standards. First-generation distillation systems in biofuels processing were implemented when simplicity was highly prized—thus the environmental concerns related to energy usage were largely relegated to minimizing associated emissions. Production was valued over minimizing the total process energy consumed or the impact of process inefficiencies on the environment. Today, policies and regulatory initiatives targeting the reduction of greenhouse-gas emissions are impacting consumers and producers of energy, creating incentives for improving energy efficiency and minimizing environmental footprints.

Examples of regulation impacting energy consumers and producers include California's Low Carbon Fuel Standard (LCFS) and the U.S. EPA's Clean Power Plan. The LCFS models fuel pathways to assign a Carbon Intensity (CI) to fuels, reflecting a fuel's lifecycle carbon dioxide emissions. A fuel producer's pathway, reflecting the CI for their process, generates credits or requires the purchase of credits from other producers to meet California's CI targets. These credits are traded on an exchange that establishes their value and permits monetization by producers. Improvements in process energy efficiency are directly rewarded through the LCFS system, incentivizing investments in energy efficiency. Energy-efficient systems are desired because the LCFS incentives directly reward producers for reducing their energy requirements, even when low energy prices provide little or no incentive to make such investments.

In view of the foregoing challenges, what are needed are improvements in overall energy efficiency and optimization for new or existing biorefineries employing distillation and/or co-product drying.

SUMMARY OF THE INVENTION

Some variations of the invention provide a method of energy-efficient drying of a wet material in a biorefinery, the method comprising:

(a) providing a wet material containing a liquid phase of a first product, a solid phase of a co-product, and water;

(b) thermally treating the wet material to obtain a process vapor containing the first product and a process liquid containing the co-product;

(c) increasing the pressure of the process vapor;

(d) heating at least a portion of the process liquid in an indirect dryer by condensing the process vapor that is out of contact with the process liquid, whereby heat of condensation of the process vapor is utilized for drying the process liquid;

(e) recovering a dryer exhaust stream derived from drying the process liquid; and (f) optionally, separating the dryer exhaust stream into an exhaust vapor stream and an exhaust solids stream.

In some embodiments, at least a portion of the dryer exhaust stream or, if step (f) is conducted, the exhaust vapor stream, is compressed and returned to step (b) to provide heat for thermally treating the wet material, thereby recovering heat contained in the dryer exhaust stream. In certain embodiments, step (c) together with the dryer exhaust stream or the exhaust vapor stream being compressed and returned to step (b), forms a recompression loop, and at least 50%, 60%, 70%, 80%, 90%, 95%, 99%, or essentially all of the thermal energy demand of the biorefinery is provided by the recompression loop.

When step (f) is conducted, at least a portion of the exhaust vapor stream may be compressed and used to heat another stream within the biorefinery, thereby recovering heat contained in the exhaust vapor stream. For example, a second process vapor may be generated from another stream, wherein the second process vapor is compressed and fed to a second indirect dryer, and wherein heat of condensation of the second process vapor is utilized for drying within the second indirect dryer acting as an additional effect. The second indirect dryer further dries the co-product. In this configuration, the (first) indirect dryer in step (d) is an effect within a multiple-effect heat-exchange system.

When step (f) is conducted, at least a portion of the exhaust vapor stream may be condensed in a process stream containing the same components as the exhaust vapor stream, to reduce the amount of the exhaust vapor stream being emitted to the atmosphere. Alternatively, or additionally, at least a portion of the exhaust vapor stream, or a compressed form thereof, may be condensed using an out-of-contact heat exchanger, to reduce the amount of the exhaust vapor stream being emitted to the atmosphere.

In preferred embodiments, step (b) utilizes distillation. In preferred embodiments, step (c) utilizes mechanical vapor recompression, thermal vapor recompression, or a combination thereof.

In some embodiments, in step (d), the process liquid is also heated with process steam that is out of contact with the process liquid, wherein the heat of steam condensation and the heat of condensation of the process vapor are co-utilized for drying the process liquid.

The method may further include recovering, from the indirect dryer, a condensed form of the process vapor in a product stream. The method may further include recovering, from the indirect dryer, a dried form of the co-product. In certain embodiments, the biorefinery is an ethanol plant, the first product is ethanol, and the co-product is dried distillers grains.

Other variations of the invention provide a method of energy-efficient drying of a wet material in a biorefinery, the method comprising:

(a) providing a wet material containing a liquid phase of a first product, a solid phase of a co-product, and water;

(b) thermally treating the wet material to obtain a process vapor containing the first product and a process liquid containing the co-product;

(c) heating at least a portion of the process liquid in an indirect dryer by condensing the process vapor that is out of contact with the process liquid, whereby heat of condensation of the process vapor is utilized for drying the process liquid;

(d) recovering a dryer exhaust stream derived from drying the process liquid; and (e) separating the dryer exhaust stream into an exhaust vapor stream and an exhaust solids stream, wherein at least a portion of the exhaust vapor stream is compressed and returned to step (b) to provide heat for the thermally treating, thereby recovering heat contained in the dryer exhaust stream.

In some embodiments of these methods, at least a portion of the exhaust vapor stream is compressed and used to heat another stream (besides thermally treating the wet material) within the biorefinery, thereby recovering additional heat contained in the exhaust vapor stream.

In some embodiments, the method further includes recovering, from the indirect dryer, (a) a condensed form of the process vapor in a product stream (e.g., ethanol) and (b) a dried form of the co-product (e.g., dried distillers grains).

Some variations of the invention provide a system for energy-efficient drying of a wet material in a biorefinery, the system comprising:

(i) a thermal-treatment unit configured for separating a wet material into a process vapor stream and a process liquid stream, wherein the wet material contains a liquid phase of a first product, a solid phase of a co-product, and water, wherein the process vapor stream contains the first product, and wherein the process liquid stream contains the co-product;

(ii) a first compressor in flow communication with the process vapor stream of the thermal-treatment unit, wherein the first compressor is configured for increasing the pressure of the process vapor stream;

(iii) an indirect dryer in flow communication with the first compressor, wherein the indirect dryer is configured to heat the process liquid stream by condensing the process vapor stream, whereby heat of condensation of the process vapor stream is utilized for drying the process liquid stream, and wherein the indirect dryer is configured with a dryer exhaust stream as an output; and (iv) optionally, a dryer-exhaust separation unit configured to separate the dryer exhaust stream into an exhaust vapor stream and an exhaust solids stream.

In some system embodiments, the thermal-treatment unit is one or more distillation columns. In some embodiments, the first compressor is a mechanical vapor recompression unit or a thermal vapor recompression unit. The indirect dryer may be part of a multiple-effect heat-exchange subsystem.

Some systems further comprise a second compressor in flow communication with the dryer exhaust stream or, if the dryer-exhaust separation unit is present, with the exhaust vapor stream. The second compressor may be configured for increasing the pressure of the exhaust vapor stream, the process vapor stream, or both exhaust vapor stream and process vapor stream.

In some embodiments, the second compressor is a mechanical vapor recompression unit or a thermal vapor recompression unit.

When the dryer-exhaust separation unit is present, the system may comprise an out-of-contact heat exchanger in flow communication with the exhaust vapor stream, or a compressed form thereof. Alternatively, or additionally, the system may comprise a second indirect dryer that is configured to further dry the co-product.

Figure 1:
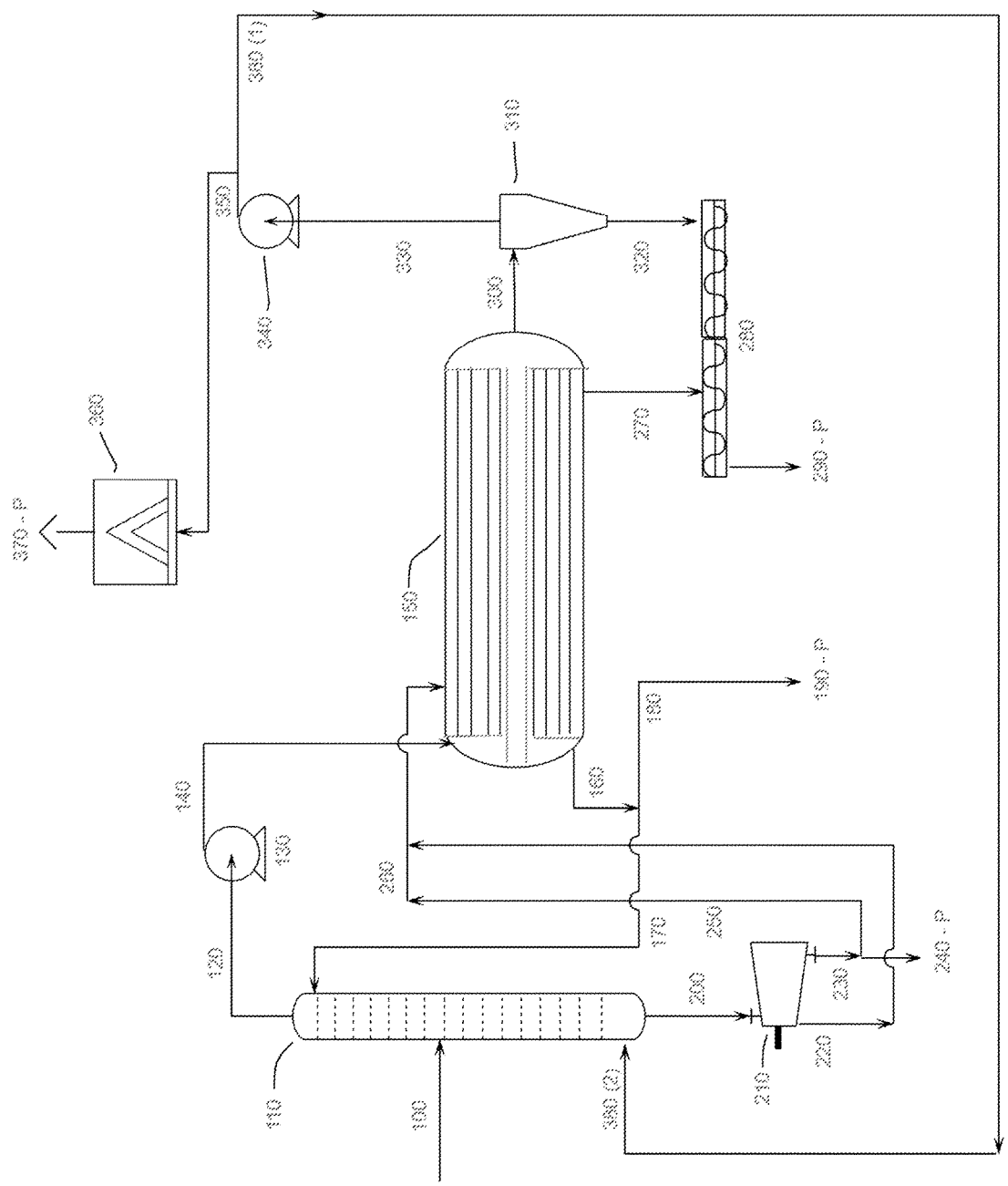
FIG. 1 depicts an exemplary process flow for a biorefinery with product distillation and co-product drying, wherein compressed distillation vapor is used, rather than steam, to dry the co-product, and wherein the exhaust from drying is compressed and returned to drive distillation, forming a compression loop that reduces overall energy usage.

These and other embodiments, features, and advantages of the present invention will become more apparent to those skilled in the art when taken with reference to the following detailed description.

DETAILED DESCRIPTION OF EMBODIMENTS OF THE INVENTION

Certain embodiments of the present invention will now be further described in more detail, in a manner that enables the claimed invention so that a person of ordinary skill in this art can make and use the present invention. All references herein to the "invention" shall be construed to refer to non-limiting embodiments disclosed in this patent application.

Unless otherwise indicated, all numbers expressing conditions, concentrations, yields, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in its respective testing measurements.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. If a definition set forth in this section is contrary to or otherwise inconsistent with a definition set forth in patents, published patent applications, and other publications that are incorporated by reference, the definition set forth in this specification prevails over the definition that is incorporated herein by reference.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

The present invention is premised on energy integration for improving the energy efficiency of biorefineries or other process plants. In some variations, a method is disclosed for improving the energy efficiency of drying operations through integration of a dryer that utilizes the heat of condensation of process vapors alone, or in combination with process steam, to dry material whose emissions are captured and directed to a process where heat of condensation of the process vapors may be utilized.

Tube dryers are conventionally used in series to progressively dry materials with the material discharged from earlier-stage dryers feeding later stages where further drying is accomplished. In these designs, each dryer condenses steam with the condensate returned to a steam generator for reheating and conversion back into steam. The recovery and reuse of the steam raised from drying has not been used in biorefineries, since the conventional methods of drying driven by heated air cannot easily nor efficiently be used as cascaded heat in distillation. Variations of the present invention utilize recovery of process vapor heat of condensation by employing process vapor rather than process steam to operate an indirect dryer, thereby improving overall process energy efficiency. An "indirect dryer" means that the material being dried is heated indirectly from a heating medium, rather than directly (physical mixing).

In particular, the indirect dryer employed herein condenses vapors using a cooling medium (e.g., water contained in the wet material) on the outside of tubes, but using process vapors rather than steam alone to transfer heat to the wet material undergoing drying. This heat vaporizes liquid in the wet material. The resulting vapors, which contain volatilized liquid product and potentially volatilized organic compounds, volatilized inorganic compounds, and suspended or entrained solids, are directed to (a) a process stage that requires heat and minimizes the need for vapor cleanup or to (b) an out-of-contact heat exchanger that produces vapors for process use or to (c) another dryer, acting as an additional effect, or a combination thereof.

Indirect dryers disclosed herein may also form multiple effects that cascade heat from dryers condensing higher pressures and temperatures to dryers condensing lower pressures and temperatures of steam and/or process vapors. The indirect dryer may separate clean process vapors and steam from vapors containing volatile organic compounds and entrained materials, and return heat in a manner that minimizes the need for vapor cleanup and system cleaning requirements.

In some embodiments, an indirect dryer employs a rotary steam-tube dryer design, except that a process vapor (comprising something other than water) rather than steam is condensed. The drying is accomplished by the heat of vaporization. In some embodiments, tube dryers are employed with a bundle of tubes inside the dryer, and the dryer body has little or no air for assisting in the drying. A tube dryer generally operates at a lower temperature than other dryers and rotates at a slower speed. Material tumbles gently around the tubes that rotate with the shell.

The concept of mechanical vapor compression in distillation has been deployed in reducing process requirements in refining for many decades. It has also been widely deployed in water desalination and process evaporation. Mechanical vapor compression, when used in distillation, recycles the heat of distillation by a closed heat pump, as disclosed, for example, in U.S. Pat. Nos. 4,340,446, 4,422,903, 4,539,076, 4,645,569, 4,692,218, 4,746,610, 5,294,304, 7,257,945, 8,101,217, 8,101,808, 8,114,255, 8,128,787, 8,283,505, 8,304,588, 8,535,413, and 8,614,077, which are hereby incorporated by reference herein. Thermal vapor compression, when used in distillation, evaporation, dehydration, and drying, recycles latent heat by a closed heat pump, as disclosed for example in U.S. Pat. Nos. 5,772,850, 4,536,258, and 4,585,523, which are hereby incorporated by reference herein. These methods of energy recovery have been rarely utilized, however, in the distillation processes of bio-fermentation producers.

In this disclosure, mechanical vapor recompression (MVR) and/or thermal vapor recompression (TVR) are preferably used to produce vapor that meets conditions to best integrate and optimize energy recovery between processes, and to reduce overall process thermal energy usage in the biorefinery. The heat of condensation of the compressed vapors provides energy to the receiving process stage, such as drying. Heat exchangers utilizing multiple effects, thermal vapor recompression, and/or mechanical vapor recompression are used to balance process conditions by increasing or decreasing vapor energy to serve process design requirements. The number of dryer effects and the integration of MVR/TVR will depend upon cost and design requirements for the integrated system of interest.

All instances of "vapor compression," "vapor recompression," MVR, TVR, MVR/TVR, and the like mean mechanical vapor recompression, thermal vapor recompression, or a combination thereof. Thermal vapor recompression may also be referred to as thermocompression or steam compression.

A wide variety of industries process materials that require drying. Current dryer designs transfer heat through convection by contact with a gas that has been heated to a temperature higher than that of the material to be dried, through conduction by contact with a solid material hotter than the material to be dried, or through radiant heat transfer which heats material by transferring energy via electromagnetic waves, such as infrared, microwave, etc. A common characteristic of each of these methods is that they transfer energy to the material from process steam created in a boiler or electricity, which is also usually created from driving an electrical generator with steam that was created in a boiler.

Many processing facilities include condensers that are used to cool vapors sufficiently to condense them into a liquid. The cooling water in such condensers circulates between the condenser and cooling towers or an air-cooled heat exchanger. Because the vapors do not contain enough energy to be effectively reused in the facility's process, the heat of condensation is conventionally lost. By upgrading these process vapors through mechanical vapor recompression or thermal vapor recompression, if needed, or directly transferring the vapors without pressure increase to a dryer where the process vapors can be condensed, the heat of condensation that would otherwise be lost in the condenser can be utilized. Another method for recapturing the heat of condensation employs a plurality of dryers as multiple effects (or a single dryer configured with multiple-stage effects) in which the heat otherwise lost in dryer exhaust is directed to another dryer, either directly or through vapor generation via a heat exchanger.

As an example of the general principles taught herein, a distillation process may be combined effectively with a drying process. The following description is directed to typical ethanol plant distillation, dehydration, evaporation, and distillers-grains drying as a non-limiting example of the disclosed method and system. All instances of "distillery" in this specification may be replaced with "biorefinery" and vice-versa.

It will be understood by a skilled artisan that the present invention is by no means limited to the biorefinery being an ethanol plant. The principles disclosed herein may be applied to a wide variety of industrial processes such as wood pulp processing, food processing, brewing, and mineral processing, for example.

In addition, as will be appreciated by a person of ordinary skill in the art, the principles of this disclosure may be applied to many biorefinery configurations beyond those explicitly disclosed or described in the drawings hereto. Various combinations are possible and selected embodiments from some variations may be utilized or adapted to arrive at additional variations that do not necessarily include all features disclosed herein. In particular, while some embodiments are directed to ethanol as the primary biofuel/biochemical, the present invention is by no means limited to ethanol. For example, the invention may be applied to ABE fermentation producing a mixture of acetone, n-butanol, and ethanol. One or more additional distillation or other separation units may be included to separate components of a fermentation mixture. Also, in some embodiments, the primary product is less volatile than water (at atmospheric pressure), rather than more volatile, as is the case with ethanol. An example of a biofuel/biochemical less volatile than water is isobutanol.

Most distillation processes heat beer fed to a distillation column with steam to raise its temperature to the beer's boiling point and then continue to add energy with steam as needed to overcome the beer's heat of evaporation or latent heat, converting the ethanol in the beer into vapors. Ethanol's lower boiling point (versus water) causes the ethanol to vaporize and exit the top of the distillation column. The solids in the beer, along with water and other liquids with boiling points higher than that of ethanol, are collected in the bottom of the distillation column and then transferred to a centrifuge where a wet cake containing solids and a significant proportion of liquids is separated from a liquid centrate. This wet cake is typically transferred to a dryer where the solids are dried to a moisture level appropriate for storage and shipping. Meanwhile, the alcohol vapors exiting the top of the distillation column are typically directed to a water-cooled condenser where they condense, transferring their heat of condensation to condenser cooling water prior to transfer of the condensate to a dehydration process for final upgrading to a marketable ethanol product (as required by azeotropic limitations in making high-purity ethanol).

In variations of the present invention, the ethanol process vapor is redirected compared to conventional operations. Rather than being sent to a condenser, the process vapor is sent to a dryer, such as a steam tube dryer. A steam tube dryer is conventionally heated solely by process steam, but in the process herein the tube dryer (or other indirect dryer) is heated by process vapor. The ethanol vapors are condensed within the indirect dryer and the process-vapor heat of condensation is transferred to the wet cake, rather than being lost to condenser cooling water. The condensed alcohol vapors may then be transferred as a liquid to the dehydration process as they would have been if they had been condensed in a condenser. The vaporized liquid removed from the wet cake is transferred to the distillation column where the heat of condensation (of the vaporized liquid) is recovered directly or through condensation in a heat exchanger and used to vaporize ethanol in the beer feed. Alternatively, or additionally, the vaporized liquid may be transferred to another dryer and condensed, recapturing the heat of condensation for use in further drying.

An important benefit in some embodiments is the separation between relatively clean and relatively dirty vapors. The vapors exiting the top of the distillation column are relatively clean and may be condensed in the tubes of a dryer with minimal concern for deposits building up in the tubes, requiring periodic cleaning. The vapors exiting the dryer are relatively dirty, but they may used to heat beer which is much dirtier, where "dirty" means the presence of contaminants that might form deposits or contaminate process flows and necessitate periodic cleaning or treatment. The dryer exhaust may also be directed to an out-of-contact heat exchanger or reboiler where the dirty exhaust condenses on one side of the heat exchanger, passing the heat to a clean medium that may be used to supplement steam generation or drive a cascaded tube dryer. Conventionally, emissions from dryers require treatment through subjection to high temperatures for the time required to oxidize volatile organic compounds in a thermal oxidizer. By condensing these emissions in a distillation column, the quantity of vapors requiring treatment through thermal oxidation is minimized, if not eliminated. Considerable value may be realized through recovery of previously lost energy and elimination of both equipment and inefficient treatment of dryer emissions.

In other applications, the method and system may be applied by identifying points in a facility's process where significant latent heat is lost through condensers and bypassing those condensers to recover the latent heat by condensing vapors in a dryer. Also, system designs may be optimized through identification of clean and dirty process vapor streams that may be condensed in a process block that minimizes treatment requirements and integrates with dirty dryer emissions and clean dryer heating vapors.

In one aspect, a method and system for drying materials is provided, in which a condensing dryer is integrated with other plant processes to recover the heat of condensation of clean process vapors for use in drying, and contaminated dryer exhaust is returned to processes directly or indirectly via an out-of-contact heat exchanger for recovery of the dryer exhaust's heat of condensation.

In another aspect, mechanical vapor recompression and/or thermal vapor recompression assists in recovering the heat of condensation from vapors produced in distillation and drying, providing a reduction in process thermal energy by the addition of mechanical energy for driving the mechanical recompression.

In another aspect, mechanical vapor recompression and/or thermal vapor recompression is sized or operated to match the thermal energy required in distillation with the thermal demand operated within the drying, and vice-versa, resulting in a reduced energy demand as a result of the reduction in standard steam energy demand due to energy recovered by mechanical vapor recompression and/or thermal vapor recompression in the distillation and drying.

In another aspect, the dryer is sized or operated to match steam demand in the distillation process with the mechanical vapor recompression and/or thermal vapor recompression adjusting the total thermal energy demand of the biorefinery in order that some or all of the thermal energy is provided by the recompression loop between the dryer and the distillation processes.

In another aspect, the portion of the dryer exhaust consisting of steam with volatile organics requiring treatment is minimized by condensing the vapors in a process stream of similar composition and minimizing the amount of dryer exhaust gas produced by evaporation of liquids from the material being dried.

In another aspect, the portion of the dryer exhaust consisting of steam with volatile organics requiring treatment is minimized by condensing the vapors in an out-of-contact heat exchanger and minimizing the amount of dryer exhaust gas produced by evaporation of liquids from the material being dried.

In another aspect, the portion of the dryer exhaust consisting essentially of steam condenses in an out-of-contact heat exchanger and the dryer exhaust gas produced by evaporation of liquids from the material being dried is compressed to drive an additional tube dryer that increases the amount of water removed from the stillage coproducts of the fermentation.

In another aspect, mechanical vapor recompression and/or thermal vapor recompression is added to a biorefinery where the heat of vaporization in the distillation top product is passed to a dryer with vapor recompression used, if necessary, to raise steam pressures and/or temperatures to drive the distillation process, thereby completing the vapor recompression loop for the distillation.

In another aspect, mechanical vapor recompression is applied to a distillation top product that is used for drying and mechanical vapor recompression is applied to dryer vapor exhaust to compress it and return it to distillation.

In another aspect, mechanical vapor recompression is applied to a distillation top product that is used for drying and thermal vapor recompression is applied to dryer vapor exhaust to compress it and return it to distillation.

In another aspect, thermal vapor recompression is applied to a distillation top product that is used for drying and mechanical vapor recompression is applied to dryer vapor exhaust to compress it and return it to distillation.

In another aspect, thermal vapor recompression is applied to a distillation top product that is used for drying and thermal vapor recompression is applied to dryer vapor exhaust to compress it and return it to distillation.

Figure 2:
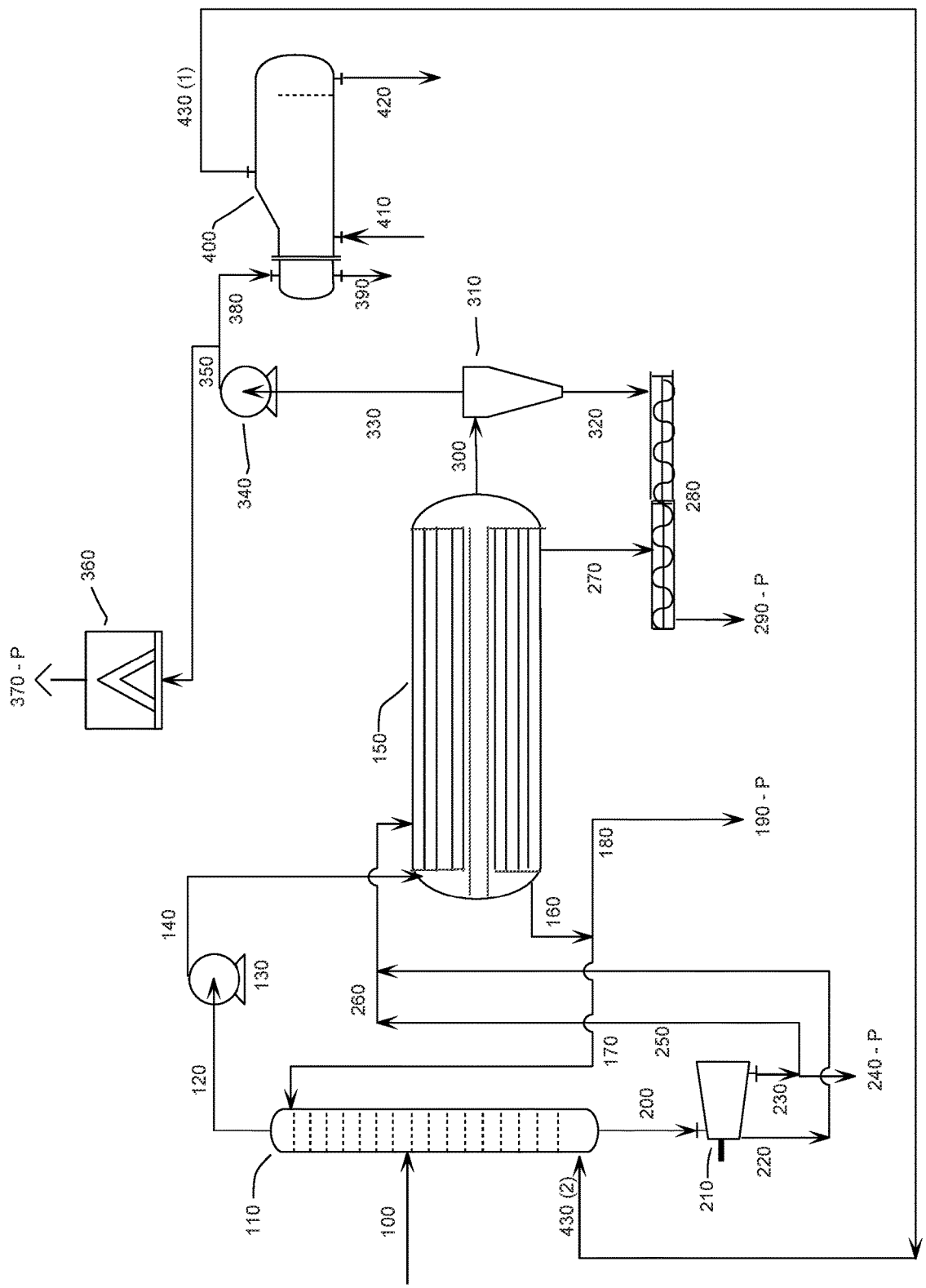
FIG. 2 depicts an exemplary process flow for a biorefinery with product distillation and co-product drying, wherein compressed distillation vapor is used, rather than steam, to dry the co-product, and wherein the exhaust from drying is passed to an out-of-contact heat exchanger or reboiler to recover the dryer heat as steam that is returned to drive distillation, forming a compression loop that reduces overall energy usage.
Figure 3:
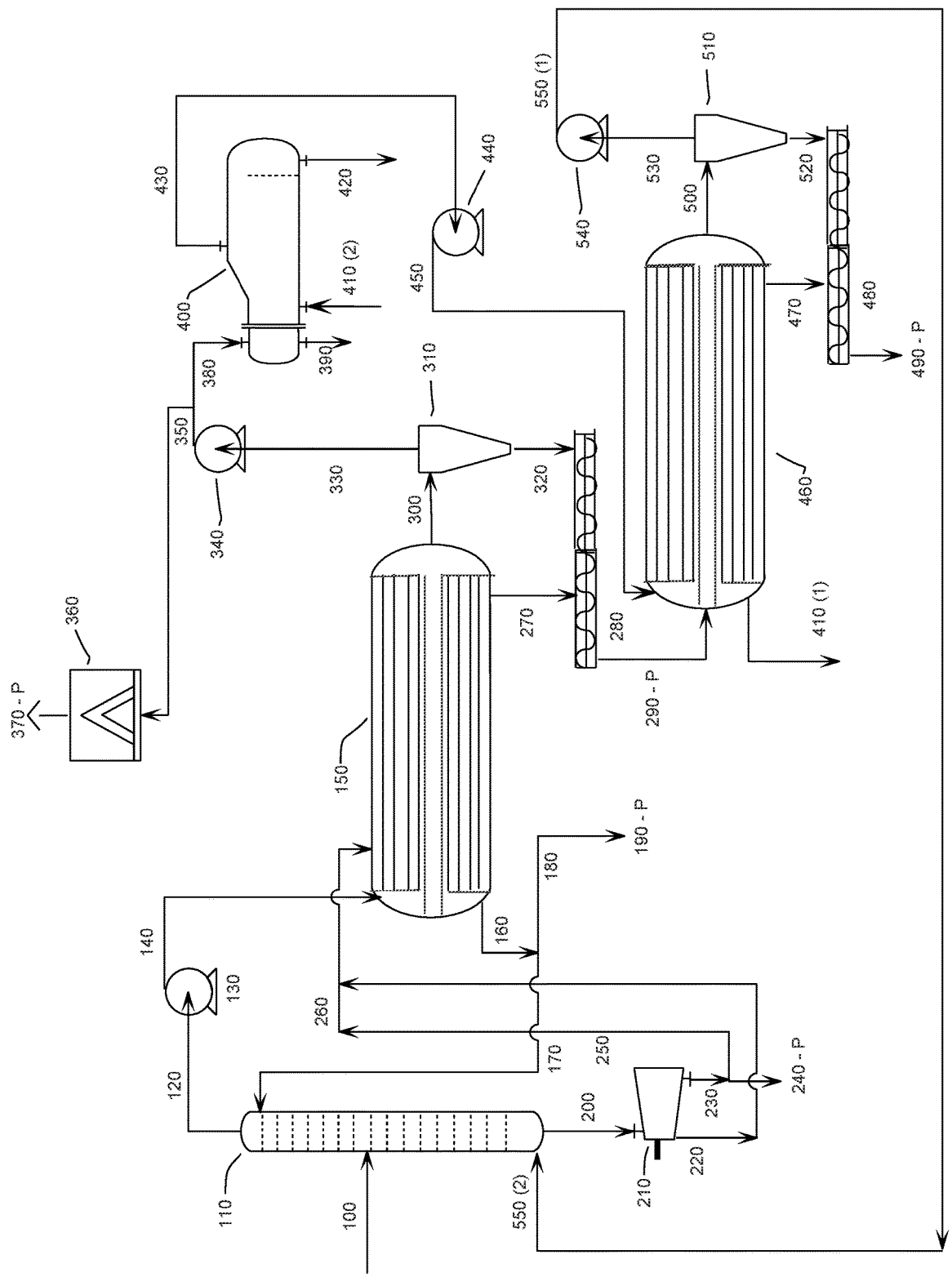
FIG. 3 depicts an exemplary process flow for a biorefinery with product distillation and co-product drying, wherein compressed distillation vapor is used, rather than steam, to dry the co-product, and wherein the exhaust from drying is passed to an out-of-contact heat exchanger or reboiler to drive an additional steam tube dryer in a cascaded configuration for additional drying capacity, forming a compression loop that reduces overall energy usage.

The schematic drawings, FIG. 1, FIG. 2, and FIG. 3, depict examples of process flows for a biofuels plant with distillation and drying processes that are energy-integrated. These diagrams show a distillation process used for purification of a biofuel, such as ethanol, and the drying of fermentation co-products, such as dried distillers grains.

As described in more detail below including with reference to drawing elements, the process of FIG. 1 includes distillation of beer feed with distillation vapors being compressed and transferred to an out-of-contact wet cake dryer. The bottom product of the distillation is fed to a centrifuge where the coarse solids are separated as a wet cake and sent to the dryer, and the fine-soluble components are split into a stillage product, part of which is sent to the dryer with the wet cake, while the balance of the stillage is returned and reused in the biofuels plant. The dryer, while condensing the vapors from the distillation, generates steam-containing vapors as the stillage in the wet cake is evaporated. The steam-containing vapors are then compressed and transferred to the beer column to drive the distillation process. A portion of the steam-containing vapors from the dryer is passed to a thermal oxidation system for the removal of volatile organic components. A recompression loop is formed between the vapors of the distillation column sent to the dryer-condenser and the dryer vapor exhaust which is compressed to conditions effective for reuse in the distillation stage.

The schematic drawing FIG. 2 depicts a process in which the exhaust from the dryer is compressed prior to passing the dryer's heat to an out-of-contact heat exchanger or reboiler where the dryer heat is recovered as steam used to drive the distillation.

The schematic drawing FIG. 3 depicts a process in which the exhaust from the dryer is compressed prior to passing the dryer heat to an out-of-contact heat exchanger as a reboiler where the dryer heat is recovered as steam and used to drive an additional steam tube dryer in a cascaded configuration. The cascaded heat multiplies the heat reuse, thereby providing additional drying capacity. The cascaded dryer exhaust from the final dryer in the series is compressed for use in driving the distillation process.

In some embodiments, the amounts of thermal energy required to sustain the distillation and drying stages are nearly equal in magnitude; therefore, the raised steam by the dryer may be compressed and fully or partially reused to support the distillation stage.

FIGS. 1-3 depict bio-fermentation distillery and drying process stages which generally include the following stages:

(1) a distillation stage, where the fermented products are processed and the biochemical top products are separated from the fermentation water and distillers grains co-products;

(2) a condensation stage where the vapors from distillation stage 1 are passed on to a drying system where the heat of distillation is lost to cooling water or where the vapors are compressed to recover the heat of distillation for use in dryer stage 4;

(3) a stillage handling stage for the bottom product of distillation stage 1 in which a centrifuge dewaters the co-products and the recovered wet co-products of the fermentation pass to dryer stage 4;

(4) a dryer stage for the biochemical dewatered co-products from the bottoms of distillation stage 1, in which the wet cake is dried sufficiently to achieve a long shelf life as a stable feed product and the raised vapors in the exhaust of the dryer pass into a compressor where the exhaust steam goes to drive distillation stage 1 and a portion is discarded, if necessary, through thermal oxidation stage 5 in which volatile co-products are destroyed; and (5) a thermal oxidation stage, where volatile biochemical components of fermentation are destroyed prior to the gasses being emitted to the atmosphere.

The general distillery process includes stages which all require energy in the form of thermal energy and/or mechanical/electrical energy. The schematic diagrams (FIGS. 1-3) highlight the post-fermentation stages of distillation and drying where the finished products are brought to marketable quality. The thermal energy required in a plant without vapor recompression in distillation and without vapor recompression in drying can be off-set and replaced by the energy required for driving the vapor recompression as depicted in FIGS. 1-3.

The process energy distribution in the distillation and drying processes of the distillery, as defined in stage 1 above, is adjusted as needed through the use of vapor recompression (MVR and/or TVR) to supply the thermal energy required for drying stage 4. Vapor recompression (MVR and/or TVR), in turn, passes a sufficient portion of the raised steam from dryer exhaust from stage 4 back to distillation stage 1. Distillation and drying usually represent the largest energy-consuming stages in the distillery and therefore provide the largest potential opportunity for reducing the total energy consumed in the plant.

The fermentation product entering the distillation contains the desired biochemical product as a watery solution with other co-products, passing via line 100 into the distillation system 110, where the biochemical fuel product of the fermentation is fractionated for separation of the biochemical fuel from the watery co-products. The biochemical passes as a vapor out of the distillation stage via line 120 and the watery co-products pass out of the distillation stage as a liquid via line 200.

The distillation system, 110, yields a top product which has a biochemical product composition that (in the case of ethanol as the biochemical) approaches an azeotrope with water or which may be near purity with respect to the desired biochemical. The azeotrope or nearly pure biochemical product passes out of the distillation system as vapors via the vapor line 120 to a compressor 130 (which may be a compressor system with multiple compressors and/or ancillary equipment). The compressor 130 increases the pressure and condensing temperature of the vapors as required such that the heat of vaporization represents a higher quality of heat as needed for a heat supply to the dryer system 150. In the case that the distillation is operated at sufficiently high pressure to drive the dryer without the need for additional compression, for example, compressor 130 may be omitted.

Distillation vapors of sufficient pressure, optionally compressed by compressor system 130, pass via line 140 on to the dryer system 150, wherein the vapors condense within the dryer 150, providing the heat for drying. The condensed vapors within dryer 150 are liquefied and pass out of the dryer 150 via a line 160 where the liquid condensate is split between distillation reflux via line 170 and the finished product 190-P via line 180 (the label "-P" denotes a product of the process).

The watery co-products of distillation are a bottom product leaving the distillation system 110 via the liquid line 200 passing to a centrifuge system 210 where the wet coarse solids pass via line 220 to line 260 and the remaining watery portion with soluble co-products passes via line 230 where the flow is split with a portion of the water containing dissolved co-product is recovered (or further processed) as product 240-P and the balance of the liquid passes to line 250, which is combined with line 220 into line 260 and on to the dryer 150.

The dryer 150 drives steam off wet cake, which steam passes out of dryer 150 via line 300, with the partially dewatered fermentable co-products, after being sufficiently dried, passing out of dryer 150 via line 270. The steam with volatile organics raised from drying the wet distillers co-products passes out of dryer 150 via line 300. The vapors raised by the dryer contain particulate solids and condensates which pass to cyclone 310 where the particulate material in the vapor stream is separated out and passes via line 320 (evaporated thin stillage or "syrup") to a conveyer system 280 together with the dried co-product from line 270 where they are combined as finished product 290-P. Optionally, some or all of stream 270 may be recovered as a dried co-product without necessarily combining with stream 320. Optionally, some or all of syrup stream 320 may be recovered as a product without necessarily combining with stream 270. Various combinations of streams 290-P, 270, 320, and 240-P may be utilized.

The extent of drying in the indirect dryer(s) may be varied as desired. Generally, the product stream 290-P may vary from about 35 wt % solids to about 95 wt % solids. In various embodiments, the product stream 290-P is about 40, 45, 50, 55, 60, 65, 70, 75, 80, 85, or 90 wt % solids. The intermediate stream 270 may also be about 40, 45, 50, 55, 60, 65, 70, 75, 80, 85, or 90 wt % solids.

The cyclone system 310 removes heavy particulate materials, passing the clean steam vapors with volatile organics via line 330 to compressor 340. The pressurized vapors from the compressor are raised to a sufficient pressure and condensing temperature to drive the distillation system 110 via line 380 (1 and 2). The vapors collected by compressor 340 pass out via line 350 where a portion is removed and transferred to thermal oxidizing system 360, if required, with the oxidized residual passing to the atmosphere as stream 370-P.

In FIG. 1, the largest portion of vapors from compressor 340 pass through line 380 (1 and 2) and drive the distillation system 110 directly. This occurs when the latent heat of the dryer exhaust is released through condensing the vapors in the distillation column. In FIG. 2, the vapors pass from compressor 340 to line 380 which passes the vapors to an out-of-contact heat exchanger 400 that condenses the vapors and transfers the latent heat recovered, vaporizing a process liquid passed to the heat exchanger via line 410. The generated vapors are passed via line 430 (1 and 2) to the distillation column 110 with excess process liquid blow down passed via line 420. In FIG. 3, the vapors pass from out-of-contact heat exchanger 400 via line 430 to compressor 440, then to line 450 that passes high-pressure vapors to an additional tube dryer 460. The compressed vapors in tube dryer 460 capture the heat of condensation to drive the dryer with the condensate passing back to an out-of-contact heat exchanger 400 via line 410 (1 and 2). In the embodiment of FIG. 3, the partially dried distillers cake and syrup, 290-P, from tube dryer 150, enter the additional tube dryer 460, where the dried distillers grains pass via line 470 to material handling 480 resulting in product 490-P. The generated steam vapors in the exhaust from tube dryer 460 pass via line 500 to cyclone 510 with dryer dust passing via line 520 to material handling 480 and the exhaust vapors passing via line 530 to compressor 540. The compressed steam vapors from compressor 540 pass via line 550 (1 and 2) to distillation system 110.

The steam driving distillation system 110 is delivered directly via line 380 (1 and 2) in FIG. 1 and indirectly via line 430 (1 and 2) from heat exchanger 400 in FIG. 2. In both FIG. 1 and FIG. 2, and indirectly via line 550 (1 and 2) from additional tube dryer 460 exhaust, the vapors are sourced from dryer system 150 and compressor 340 increases the pressure and condensing temperature as required to meet process conditions for use in distillation system 110. In FIG. 3, the vapors are sourced from the additional tube dryer 460, having compressed steam vapors from out-of-contact heat exchanger 400, which is driven from compressed steam vapors from the exhaust of tube dryer 150. The biofuels vapors from distillation system 110 may have the pressure and condensing temperature increased, if needed, by compressor 130 for use in dryer 150. In FIG. 1 and FIG. 2 the two compressors, 130 and 340, form a complete recompression loop wherein the latent heat of distillation is driven through the dryer cycle and returned to the distillation. In FIG. 3 the three compressors, 130, 340, and 540, form a complete recompression loop wherein the latent heat of distillation is driven through the dryer cycle and returned to the distillation.

In some embodiments, compressors 130 (FIGS. 1-3), 340 (FIGS. 1-3), and/or 540 (FIG. 3) are not present, such as when the distillation heat is directly cascaded, or when distillation pressure is sufficient such that further pressure increase of vapor is not necessary.

In the process depicted in FIGS. 1-3, there are various stream splits. One skilled in the arts of biorefinery design/operation or chemical engineering will be able to determine the split fractions in order to achieve the desired process outcome, while maintaining mass balance. The process may be simulated to determine split ratios that best achieve the desired energy integration.

For example, liquid condensate in line 160 is split between line 170 (distillation reflux) and line 180 (product). The ratio of line 170 flow rate to line 180 flow rate is the reflux ratio. In principle, the reflux ratio may be 0 when no liquid condensate is returned to the column (e.g., under a dynamic situation such as during column maintenance); the reflux ratio may be infinite when all liquid condensate is returned to the column (e.g., total reflux under a dynamic situation such as plant start-up). At steady state, a typical range of reflux ratios by mass is about 0.1 to 1, such as about 0.2 to 0.8, but this will vary depending on the product, process configuration, and beer quality. For ethanol, a typical range of reflux ratios is about 0.3 to 0.7, such as about 0.50 to 0.66. Higher-quality beer streams generally allow for lower reflux ratios. For biofuels other than ethanol, depending on purity requirements and other factors, very high reflux ratios may be useful, such as about 1, 2, 3, 4, 5, or even higher. Also, in certain embodiments, a relatively high reflux ratio may be employed in order to operate distillation above the optimum for the purpose of cascading a desired amount of heat to the indirect dryer.

Another example of a flow split in FIGS. 1-3 is the split of line 230 (water plus soluble co-products) splitting into line 250 (conveying to indirect dryer) and product 240-P. The split ratio by mass of line 250 to 240-P may vary, such as from 0 to about 10, e.g. about 0.1, 0.2, 0.5, 1, 2, 3, 4, or 5.

Another example of a flow split in FIGS. 1-3 is the split of line 350 into line 380(1) (or line 380 in FIGS. 2 and 3) versus that line going to the thermal oxidizing system 360. The split fraction may be 0, i.e. all material going back to distillation, directly or indirectly, and no material going to the thermal oxidizing system 360. In other embodiments, the split fraction by mass may be about 0.1, 0.2, 0.3, 0.4, or 0.5, for example, calculated as the mass flow to the thermal oxidizing system 360 divided by the mass flow of line 380(1) in FIG. 1 or line 380 in FIG. 2 or 3.

In should be noted that regarding FIGS. 1 to 3, specific unit operations may be omitted in some embodiments and in these or other embodiments, other unit operations not explicitly shown may be included. Various valves, pumps, meters, sensors, sample ports, etc. are not shown in these block-flow diagrams. Additionally, multiple pieces of equipment, either in series or in parallel, may be utilized for any unit operations. Also, solid, liquid, and gas streams produced or existing within the process may be independently recycled, passed to subsequent steps, or removed/purged from the process at any point.

In certain embodiments, a combined heat and power (CHP) sub-system is included in the overall system. An optional CHP sub-system has a CHP engine and is configured to provide mechanical, electrical, and/or thermal energy for driving vapor compression, wherein the CHP sub-system and vapor compression may be integrated and configured so that residual waste heat of the CHP engine offsets process thermal energy usage in the biorefinery.

For example, an MVR unit may be configured with a standard steam generator to reduce thermal energy required in the distillation. The optional CHP engine may be sized in concert with (i) mechanical demand of the MVR unit and (ii) thermal energy demand of the biorefinery. The waste heat recovered by a CHP system optionally provides at least some of the thermal energy demand of the biorefinery, and may drive an optional TVR unit.

As another example using CHP, a TVR unit may be configured with a standard steam generator to reduce thermal energy required in distillation. The optional CHP engine may be sized in concert with (i) thermal demand of the TVR unit and (ii) thermal energy demand of the biorefinery. The waste heat recovered by a CHP system optionally provides at least some of the motive vapor to drive a TVR vapor jet and/or provide for the thermal energy demand of the biorefinery.

The present invention also provides a process comprising, or adapted for, any of the disclosed methods. The biofuel or biochemical may be selected from the group consisting of methanol, ethanol, 1-propanol, 2-propanol, n-butanol, isobutanol, 2-butanol, tert-butanol, acetone, and combinations thereof. The biofuel or biochemical may also be selected from organic acids, such as lactic acid, higher alcohols (e.g., $C_{5+}$ alcohols), alkanes, etc. As used herein, "biofuel," "biochemical," biofuel/biochemical" and the like shall refer to one or more fermentation products of interest. Co-products include, but are not limited to, dried distillers grains (DDG), dried distillers grains with solubles (DDGS), still bottoms, sugars, lignin, and exported energy.

The present invention encompasses a product produced by a process comprising a disclosed method and/or a product produced by a disclosed system.

In various embodiments, the biomass feedstock may be selected from agricultural crops and/or agricultural residues. In some embodiments, agricultural crops are selected from starch-containing feedstocks, such as corn, wheat, cassava, rice, potato, millet, sorghum, or combinations thereof. In some embodiments, agricultural crops are selected from sucrose-containing feedstocks, such as sugarcane, sugar beets, or combinations thereof.

Lignocellulosic biomass may also be used as the biomass feedstock. Lignocellulosic biomass includes, for example, plant and plant-derived material, vegetation, agricultural waste, forestry waste, wood waste, paper waste, animal-derived waste, poultry-derived waste, and municipal solid waste. In various embodiments of the invention, the biomass feedstock may include one or more materials selected from: timber harvesting residues, softwood chips, hardwood chips, tree branches, tree stumps, knots, leaves, bark, sawdust, off-spec paper pulp, cellulose, corn, corn stover, wheat straw, rice straw, sugarcane bagasse, switchgrass, *miscanthus*, animal manure, municipal garbage, municipal sewage, commercial waste, grape pumice, almond shells, pecan shells, coconut shells, coffee grounds, grass pellets, hay pellets, wood pellets, cardboard, paper, carbohydrates, plastic, and cloth. Mixtures of starch-containing and/or sucrose-containing feedstocks with cellulosic feedstocks, for example, may be used.

The throughput, or process capacity, may vary widely from small laboratory-scale units to full commercial-scale biorefineries, including any pilot, demonstration, or semi-commercial scale systems. In various embodiments, the process capacity is at least about 1 kg/day, 10 kg/day, 100 kg/day, 1 ton/day (all tons are metric tons), 10 tons/day, 100 tons/day, 500 tons/day, 1000 tons/day, 2000 tons/day, 3000 tons/day, 4000 tons/day, or higher.

The biorefinery may be a retrofit to an existing plant. In other embodiments, the biorefinery is a greenfield plant.

All publications, patents, and patent applications cited in this specification are incorporated herein by reference in their entirety as if each publication, patent, or patent application was specifically and individually put forth herein. This specification hereby incorporates by reference commonly owned U.S. Pat. No. 9,925,476, issued Mar. 27, 2018, and U.S. Pat. No. 9,925,477, issued Mar. 27, 2018, and U.S. Patent App. Pub. No. 2018/0028934 A1, published Feb. 1, 2018.

In this detailed description, reference has been made to multiple embodiments of the invention and non-limiting examples and drawings relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process, when possible, as well as performed sequentially.

Therefore, to the extent that there are variations of the invention which are within the spirit of the disclosure or equivalent to the inventions found in the appended claims, it is the intent that this patent will cover those variations as well. The present invention shall only be limited by what is claimed.

What is claimed is:

1. A method of energy-efficient drying of a wet material in a biorefinery, said method comprising:
   (a) providing a wet material containing a liquid phase of a first product, a solid phase of a co-product, and water;
   (b) thermally treating said wet material to obtain a process vapor containing said first product and a process liquid containing said co-product;
   (c) optionally, increasing the pressure of said process vapor;
   (d) heating at least a portion of said process liquid in an indirect dryer by condensing said process vapor that is out of contact with said process liquid, whereby heat of condensation of said process vapor is utilized for drying said process liquid, wherein said process vapor in this step (d) is obtained from step (b) and/or step (c), if conducted;
   (e) recovering a dryer exhaust stream derived from drying said process liquid; and
   (f) separating said dryer exhaust stream into an exhaust vapor stream and an exhaust solids stream.

2. The method of claim 1, wherein at least a portion of said exhaust vapor stream is compressed and returned to step (b) to provide heat for said thermally treating, thereby recovering heat contained in said dryer exhaust stream.

3. The method of claim 2, wherein step (c) is conducted, wherein step (c) together with said dryer exhaust stream or said exhaust vapor stream being compressed and returned to step (b), forms a recompression loop, and wherein at least 50% of the thermal energy demand of said biorefinery is provided by said recompression loop.

4. The method of claim 3, wherein at least 90% of said thermal energy demand of said biorefinery is provided by said recompression loop.

5. The method of claim 3, wherein essentially all of said thermal energy demand of said biorefinery is provided by said recompression loop.

6. The method of claim 1, wherein at least a portion of said exhaust vapor stream is compressed and used to heat a separate stream within said biorefinery, thereby recovering heat contained in said exhaust vapor stream.

7. The method of claim 6, wherein a second process vapor is generated from said separate stream, wherein said second process vapor is compressed and fed to a second indirect dryer, and wherein heat of condensation of said second process vapor is utilized for drying, whereby said second indirect dryer further dries said co-product.

8. The method of claim 1, wherein at least a portion of said exhaust vapor stream is condensed in a process stream containing the same components as said exhaust vapor stream, to reduce the amount of said exhaust vapor stream being emitted to the atmosphere.

9. The method of claim 1, wherein at least a portion of said exhaust vapor stream, or a compressed form thereof, is condensed using an out-of-contact heat exchanger to reduce the amount of said exhaust vapor stream being emitted to the atmosphere.

10. The method of claim 1, wherein step (b) utilizes distillation.

11. The method of claim 1, wherein step (c) utilizes mechanical vapor recompression.

12. The method of claim 1, wherein step (c) utilizes thermal vapor recompression.

13. The method of claim 1, wherein said indirect dryer forms an effect within a multiple-effect heat-exchange system.

14. The method of claim 1, wherein in step (d), said process liquid is also heated with process steam that is out of contact with said process liquid, and wherein heat of steam condensation and said heat of condensation of said process vapor are co-utilized for drying said process liquid.

15. The method of claim 1, said method further comprising recovering from said indirect dryer a condensed form of said process vapor in a product stream.

16. The method of claim 1, said method further comprising recovering from said indirect dryer a dried form of said co-product.

17. The method of claim 1, wherein said biorefinery is an ethanol plant, wherein said first product is ethanol, and wherein said co-product is dried distillers grains.

18. A method of energy-efficient drying of a wet material in a biorefinery, said method comprising:
  (a) providing a wet material containing a liquid phase of a first product, a solid phase of a co-product, and water;
  (b) thermally treating said wet material to obtain a process vapor containing said first product and a process liquid containing said co-product;
  (c) heating at least a portion of said process liquid in an indirect dryer by condensing said process vapor that is out of contact with said process liquid, whereby heat of condensation of said process vapor is utilized for drying said process liquid;
  (d) recovering a dryer exhaust stream derived from drying said process liquid; and
  (e) separating said dryer exhaust stream into an exhaust vapor stream and an exhaust solids stream,
  wherein at least a portion of said exhaust vapor stream is compressed and returned to step (b) to provide heat for said thermally treating said wet material, thereby recovering heat contained in said dryer exhaust stream.

19. The method of claim 18, wherein at least a portion of said exhaust vapor stream is compressed and used to heat another stream within said biorefinery, thereby recovering additional heat contained in said exhaust vapor stream.

20. The method of claim 18, said method further comprising recovering, from said indirect dryer, (a) a condensed form of said process vapor in a product stream and (b) a dried form of said co-product.

* * * * *